(12) United States Patent
Farrell

(10) Patent No.: US 7,968,119 B2
(45) Date of Patent: Jun. 28, 2011

(54) TAMPER-PROOF NARCOTIC DELIVERY SYSTEM

(76) Inventor: John J. Farrell, Greenwich, CT (US)

( * ) Notice: Subject to any disclaimer, the term of this patent is extended or adjusted under 35 U.S.C. 154(b) by 621 days.

(21) Appl. No.: 10/183,678

(22) Filed: Jun. 26, 2002

(65) Prior Publication Data

US 2003/0026838 A1 Feb. 6, 2003

Related U.S. Application Data

(60) Provisional application No. 60/300,877, filed on Jun. 26, 2001, provisional application No. 60/336,052, filed on Nov. 15, 2001.

(51) Int. Cl.
*A61K 9/20* (2006.01)
*A61K 9/48* (2006.01)
*A61K 9/14* (2006.01)
*A61K 9/16* (2006.01)

(52) U.S. Cl. ........ 424/464; 424/465; 424/451; 424/490; 424/491; 424/488; 424/489

(58) Field of Classification Search .................. 424/464, 424/449, 400, 465, 451, 490, 491, 488, 489
See application file for complete search history.

(56) References Cited

U.S. PATENT DOCUMENTS

| | | | |
|---|---|---|---|
| 3,493,657 A | 2/1970 | Lewenstein et al. | 424/260 |
| 3,773,955 A | 11/1973 | Pachter | 424/260 |
| 3,896,226 A | 7/1975 | Fishman | 424/260 |
| 4,391,797 A | 7/1983 | Folkman et al. | 424/19 |
| 4,457,933 A | 7/1984 | Gordon et al. | 424/260 |
| 4,582,835 A | 4/1986 | Lewis et al. | 514/282 |
| 4,906,463 A | 3/1990 | Cleary et al. | 424/78 |
| 4,987,136 A | 1/1991 | Kreek et al. | 514/282 |
| 5,317,022 A | 5/1994 | Borsodi et al. | 514/282 |
| 5,494,677 A | 2/1996 | Giampapa | 424/426 |
| 5,496,561 A | 3/1996 | Okada et al. | 424/480 |
| 5,512,587 A | 4/1996 | Spector | 514/368 |
| 5,518,730 A | 5/1996 | Fuisz | 424/426 |
| 5,540,912 A | 7/1996 | Roorda et al. | 424/422 |
| 5,569,467 A | 10/1996 | Ruiz | 424/489 |
| 5,580,569 A | 12/1996 | Giampapa | 424/426 |
| 5,609,886 A | 3/1997 | Wantier et al. | 424/497 |
| 5,679,373 A | 10/1997 | Wick et al. | 424/448 |
| 5,698,217 A | 12/1997 | Wilking | 424/448 |
| 5,709,883 A | 1/1998 | Drizen et al. | 424/488 |
| 5,716,631 A | 2/1998 | Drizen et al. | 424/422 |
| 5,780,589 A | 7/1998 | Lazarus et al. | 530/331 |
| 5,783,583 A | 7/1998 | Simon | 514/282 |
| 5,792,477 A | 8/1998 | Rickey et al. | 424/501 |
| 5,811,451 A | 9/1998 | Minoia et al. | 514/443 |
| 5,820,877 A | 10/1998 | Yamaguchi et al. | 424/449 |
| 5,834,477 A | 11/1998 | Mioduszewski | 514/282 |
| 5,840,332 A | 11/1998 | Lerner et al. | 424/464 |
| 5,855,915 A | 1/1999 | Pinkus | 424/486 |
| 5,885,486 A | 3/1999 | Westesen et al. | 252/311 |
| 5,919,473 A | 7/1999 | Elkhoury | 424/422 |
| 5,922,705 A | 7/1999 | Simon | 514/289 |
| 5,958,452 A | 9/1999 | Oshlack et al. | 424/457 |
| 5,958,455 A | 9/1999 | Roser et al. | 424/489 |
| 5,972,954 A | 10/1999 | Foss et al. | 514/282 |
| 6,013,280 A | 1/2000 | Frisbee et al. | 424/464 |
| 6,020,002 A | 2/2000 | Myers et al. | 424/488 |
| 6,066,339 A | 5/2000 | Stark et al. | 424/489 |
| 6,068,855 A | 5/2000 | Leslie et al. | 424/468 |
| 6,130,258 A | 10/2000 | Bellos | 516/179 |
| 6,132,416 A | 10/2000 | Broselow | 604/506 |
| 6,214,379 B1 | 4/2001 | Hermelin | 424/464 |
| 6,217,911 B1 | 4/2001 | Vaugn et al. | 424/501 |
| 6,228,863 B1 | 5/2001 | Palermo et al. | 514/282 |
| 6,231,886 B1 | 5/2001 | Reder et al. | 424/449 |
| 6,261,599 B1 | 7/2001 | Oshlack et al. | 424/457 |
| 6,277,384 B1 | 8/2001 | Kaiko et al. | 424/400 |
| 6,310,072 B1 | 10/2001 | Smith et al. | 514/282 |
| 6,326,027 B1 | 12/2001 | Miller et al. | 424/468 |
| 6,335,033 B2 | 1/2002 | Oshlack et al. | 424/457 |
| 6,375,957 B1 | 4/2002 | Kaiko et al. | 424/400 |
| 6,696,088 B2 * | 2/2004 | Oshlack et al. | 424/465 |
| 2002/0010127 A1 | 1/2002 | Oshlack et al. | 514/2 |
| 2002/0058673 A1 | 5/2002 | Kaiko et al. | 514/282 |
| 2003/0124185 A1 * | 7/2003 | Oshlack et al. | 424/465 |

FOREIGN PATENT DOCUMENTS

| | | | |
|---|---|---|---|
| GB | 2282205 A | * | 3/1993 |
| WO | WO0185257 A2 | | 11/2001 |

OTHER PUBLICATIONS

"The management of constipation", National Prescribing Centre, vol. 10, No. 9, 1999.*
"Laxative-induced hypokalemic myopathy. A case history". Vierhapper et al.. Weinklin Wochenschr. Feb. 1, 1980; 92 (3): 101-3.*
Full document of the article "Laxative-induced hypokalemic myopathy. A case history". Vierhapper et al.. Weinklin Wochenschr. Feb. 1, 1980; 92 (3): 101-3.*

(Continued)

Primary Examiner — Isis A Ghali

(57) ABSTRACT

A composition for oral, transdermal or subdermal administration to a subject is described. The composition contains: (a) an agonist component; (b) an antagonist component containing at least one antagonist and having a delayed time of release; and (c) an immediate release antagonist removal component, where the subject includes a gastrointestinal tract and the antagonist removal component is present in an amount sufficient to substantially remove the antagonist component from the gastrointestinal tract of the subject before the time of release of the antagonist component. The composition may be delivered to the subject by a method which includes the step of administering the composition orally, transdermally or subdermally to the subject. When the composition of the present invention is administered orally, the method of the present invention may include the step of administering a potassium compound to the subject.

19 Claims, No Drawings

OTHER PUBLICATIONS

Mason, Barbara J., PhD, Salvato, Fernando R., MD; Williams, Lauren D., MD; Ritvo, Eva C., MD; Cutler, Robert B., PhD, "A Double-blind, Placebo-Controlled Study of Oral Nalmefene for Alcohol Dependence", Arch Gen Psychiatry, vol. 56, Aug. 1999, pp. 719-724.

Pasternak, Gavril W., "Pharmacological Mechanisms of Opioid Analgesics", *Clinical Neuropharmacology*, vol. 16, No. 1, pp. 1-18, 1993.

Yuan, Chun-Su, MD, PhD., Foss, Joseph F., MD; O'Connor, Michael, MD; Osinski, Joachim MS; Karrison, Theodore, PhD.; Jonathan Moss, MD, PhD; Roizen, Michael F., MD; "Methylnaltrexone for Reversal of Constipation Due to Chronic Methadone Use", JAMA, Jan. 19, 2000, vol. 283, No. 3, p. 367.

Carpenter, Randall L., MD; Kurz, Andrea, MD; Saleem, Rao M., MD; Sessler, Daniel I., MD; Seyedsadr, Mahmoud, PhD; Sharma, Neeru MD; and Taguchi Akiko, MD, "Selective Postoperative Inhibition of Gastrointestinal Opioid Receptors", The New England Journal of Medicine, vol. 345, No. 13, Sep. 27, 2001, p. 935.

Barr, W.H., PharmD, PhD; Carpenter, RL., MD; Nguyen, P., Russell, R., Slattery, M., Virginia Commonwealth University, Center for Drug Studies, Richmond, VA, and Adolor Corp., Malvern, PA, "ADL 8-2698 Reverses Opioid Induced Delay in Colonic Transit", American Society for Clinical Pharmacology and Therapeutics, vol. 67, No. 2, p. 91.

Joshi, G. P., Duffy, L., Chehade, J., Wesevich, J., Gajraj, N., Johnson, E. R., "Effects of prophylactic nalmefene on the incidence of morphine-related side effects in patients receiving intravenous patient-controlled analgesia," Anesthesiology, vol. 90, 1999, pp. 1007-1011.

Culpepper-Morgan, J. A., Inturrisi, C. E., Portenoy, R. K., Foley, K., Houde, R. W., Marsh, F., Kreek, M. J., "Treatment of opioid-induced constipation with oral naloxone.".

Yuan, Chun-Su, MD, PhD., Foss, Joseph F., MD; O'Connor, Michael, MD; Toledano, Alicia, ScD, Roizen, Michael F., MD; and Jonathan Moss, MD, PhD; "Methylnaltrexone prevents morphine-induced delay in oral-cecal transit time without affecting analgesia: a double blind randomized placebo-controlled trial."(Cpin, Pharmacol. Ther. 1996; 59: 469-75).

* cited by examiner

TAMPER-PROOF NARCOTIC DELIVERY SYSTEM

CROSS-REFERENCE TO RELATED APPLICATIONS

This application claims priority from U.S. Provisional Application Serial No. 60/300,877, filed Jun. 26, 2001, and from U.S. Provisional Application Serial No. 60/336,052, filed Nov. 15, 2001.

BACKGROUND OF THE INVENTION

1. Field of the Invention

The present invention relates to a tamper proof system for the delivery of narcotics to a subject. In particular, the present invention relates to a composition containing an agonist, an antagonist, and an antagonist removal component capable of removing the antagonist component from the gastrointestinal tract of the subject.

2. Background Information

Narcotic medications such as those described in U.S. Pat. No. 5,958,452, including but not limited to all drugs classified as opiates or opioids, are the most effective pain relievers available and have long been known and prescribed by the medical community for their unsurpassed analgesic effect in the human body. At the same time, however, patients taking prescribed dosages of narcotic medications exhibit a tendency to develop tolerance to and physical dependence on the prescribed medication, leading to the potential for abuse. Additionally, a distinct minority in the population has utilized and abused narcotics in an effort to attain and sustain a euphoric state that has no medical purpose. Narcotics offer fertile ground for such experimentation and subsequent addiction.

U.S. law closely regulates the availability and use of narcotics for medicinal purposes in an attempt to prevent abuse and tampering. Under the Comprehensive Drug Abuse Prevention and Control Act of 1971, specific requirements are established for record-keeping by pharmacists, formats for prescription writing, and maximum amounts of applicable drugs that can be legally dispensed. The Act further restricts prescriptions for Schedule II drugs, which include narcotics, mandating that such drug orders may not be filled or refilled without a written format. Federal law further mandates a strict accounting system to track all hospital and pharmacy dispensing of narcotics.

These barriers have no doubt restricted the opportunity for tampering and abuse by individuals of narcotics. Additionally, government-sponsored programs to aid addicted individuals (principally methadone programs) have a long history of use and some record of success. Nevertheless the problem persists of widespread and serious illegal use and abuse of narcotics manufactured for medicinal purposes.

In the past, efforts to control abuse of narcotics have included the development of drugs that incorporate an opioid antagonist, which is designed to be orally inactive and to block the analgesic effects of the opioid agonist if first dissolved and then administered parenterally. Such dosages are, however, still vulnerable to misuse and abuse by patients that resort to oral administration of multiple doses simultaneously. In addition, such dosages do not address the problem of abuse by means of nasopharyngeal routes of administration, i.e. "snorting" the drug.

Others have attempted to target and eliminate the illicit "street" extraction potential of the opioid constituent in agonist/antagonist substances by directly combining the opioid agonist and antagonist together in a unit structure. The extraction of the opioid constituent requires multiple step extraction methods not generally available to an unsophisticated street user.

While this approach may lower the tampering and abuse potential, it presents unique drawbacks. This approach predictably is forced to compromise analgesic action. Peer-reviewed literature finds that, in clinical trials, agonists acting alone yield better clinical results than comparable agonist/antagonist formulations. Studies have also shown that such combinations of agonist with antagonist create a potential for limited success in pain management. Certain patients may benefit while others experience results ranging from less efficacious pain management to limited or no therapeutic relief to slight or even profound aversion responses. Additionally, because this approach delivers a dosage of 80% agonist/10% antagonist, it is possible that the antagonist will ultimately bind all opiate receptors, completely nullifying and obstructing further delivery of intended agonist agents in protracted use by patient populations. Such a "point of saturation" represents a serious potential disadvantage to patients requiring prolonged use in cases of chronic conditions.

Several approaches which attempt to reduce tampering and prevent abuse of various opiate/opioid dosage forms have been described. These include U.S. Pat. Nos. 3,493,657, 3,773,955, 4,457,933, 4,582,835, and 6,228,863, each of which addresses one or a combination of problems present in the art. Unfortunately, the general problem of abuse of narcotic medications persists and evidence demonstrates that this problem is growing.

Several U.S. Patents have described technologies related to this invention. These include U.S. Pat. Nos. 6,214,379 and 6,020,002, which describe immediate-acting and time-released dosage forms; U.S. Pat. No. 5,958,452, which discloses a multiparticulate composition for pain management; and U.S. Pat. Nos. 5,609,886 and 6,066,339, which describe multi-component formulations. Each patent is herein incorporated by reference in its entirety. In each of these patents the selection of the components reflects the relevant chemical's ability to act effectively in a particular route of administration, as described in U.S. Pat. Nos. 5,512,587 and 5,783,583, while possessing sufficient action per dosage to independently neutralize the entire analgesic or euphoric potential of the agonist agent. However, none of these approaches provides a composition in which tampering potential can be reduced without comprising analgesic action.

U.S. Pat. Nos. 6,261,599 and 6,335,033, U.S. patent application Ser. No. 2002/0010127, and patent publication WO 01/58451 describe methods for manufacturing opioid formulations designed to release a therapeutically active agent over a period of time. However, none of these approaches provides a composition that includes an agent for the removal of an antagonist component.

There is therefore a need in the art for a composition containing an agonist and an antagonist and having reduced tampering potential while maintaining an effective analgesic action.

SUMMARY OF THE INVENTION

The above identified need in the art is met by the present invention, which in one aspect is directed to a composition for administration to a subject. The composition comprises: (a) an agonist component; (b) an antagonist component comprising at least one antagonist and having a delayed time of release; and (c) an immediate release antagonist removal component. The subject includes a gastrointestinal tract and the antagonist removal component is present in an amount sufficient to substantially remove the antagonist component from the gastrointestinal tract of the subject before the time of release of the antagonist component.

The present invention in another aspect is directed to a method for the delivery of the inventive composition to a subject, the method comprising the step of administering the composition to the subject orally, transdermally, or subdermally, wherein the composition comprises components (a), (b), and (c) as defined above.

The invention creates a tamper-proof narcotic delivery system that provides for full delivery of narcotic medication and for analgesic action on legitimate patients while at the same time effectively eliminating the problem of tampering by diversion, adulteration, or pulverization of the medication for abuse by addicts. The composition and method of the invention are of value to those practiced in the medical arts and simultaneously possess no value or utility to individuals seeking to abuse or profit from the abuse of such analgesics.

DETAILED DESCRIPTION OF THE INVENTION

The composition of the present invention may be a composition for oral administration, transdermal administration, or subdermal administration to a subject. Preferably, the composition is a composition for oral administration to a subject.

The agonist component of the present invention may be any agonist having a narcotic effect, such as, for example, an opioid agonist. The opioid agonist may be alfentanil, allylprodine, alphaprodine, anileridine, benzylmorphine, benzitramide, bupernorphine, butorphanol, clonitazene, codeine, cyclazocine, desomorphine, dextromoramide, dexocine, diampromide, dihydrocodeine, dihydromorphine, dimenoxadol, dimepheptanol, dimethylthiambutene, dioxaphetyl, butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof or mixtures thereof.

The agonist component may be either an immediate release agonist or an agonist having a delayed time of release. Preferably, the agonist component is oxycodone.

The antagonist component may be any antagonist commonly used in agonist/antagonist combinations. Preferably, the antagonist component is naltrexone, nalmefene, naloxone, or a mixture thereof.

The immediate release antagonist removal component may be an antagonist removal component capable of removing the antagonist component from the gastrointestinal tract by inducing a bowel movement in the subject. The antagonist removal component is preferably a pharmaceutical agent, a botanical agent, or a mixture thereof. More preferably, the antagonist removal component is methylnaltrexone, sennosides, bisacodyl, or a mixture thereof. Most preferably, the antagonist removal component is methylnaltrexone.

In a preferred embodiment of the composition of the invention, the agonist component and the antagonist component are present in amounts such that the time of release of the antagonist component and the time of release of the agonist component are in a ratio of at least about 4:1. As discussed in U.S. Pat. Nos. 5,540,912, 5,569,467, 5,709,883 and 5,716,631, the ratio of at least about 4:1 ensures that the agonist component is fully released and utilized four or more times sooner than the antagonist component. As exemplified in U.S. Pat. No. 5,496,561, using a 4:1 ratio ensures release of the agonist component in 12 hours while the antagonist component requires 48 or more hours to be released.

For a dermal implant, as disclosed in U.S. Pat. No. 5,580,569, or for long-term trans-dermal patch delivery systems, as described in U.S. Pat. Nos. 5,494,677, 5,518,730, 5,855,915, 6,217,911 and 6,231,886, the ratio of about 4:1 or greater for the time of release of the antagonist component to the time of release of the agonist component may be sufficient to deliver the agonist while keeping the antagonist contained for the duration of the treatment. Similarly, the ratio of about 4:1 or greater may be sufficient to deliver the agonist in an oral preparation, as disclosed in U.S. Pat. No. 4,391,797.

The immediate release antagonist removal component is included in the oral formulation to ensure that the antagonist component is removed from the body of the subject well in advance of the antagonist component reaching its scheduled time-release stage, as is also discussed in U.S. Pat. No. 4,987,136. Accordingly, the immediate release antagonist removal component acts to eliminate the antagonist component from the gastrointestinal tract of the subject in a timely fashion. Without wishing to be bound by any mechanism or theory, it is believed that the antagonist removal component functions either by directly irritating the colon muscle or by blocking opiate receptors that increase transit time in the bowel.

Maximum effectiveness of the immediate release antagonist removal component is achieved when the dietary fiber and water intake by the subject are increased.

When the composition of the present invention is administered orally, the method of the present invention may include the step of administering a potassium compound to the subject. The potassium compound may be administered orally, transdermally, or subdermally. As discussed above, administering the composition results in the removal of the antagonist component. This removal may be accomplished by a bowel movement which may be accompanied by a decrease in the level of certain electrolytes, such as potassium salts and other alkali metal salts, in the body of the subject. Administering the potassium compound is preferred for subjects that require electrolyte levels to be replenished. Such subjects may include, for example, subjects having a cardiac condition or subjects on certain medications.

As noted above, the composition of the present invention is designed to avoid release of the antagonist component. However, the antagonist component is released if the composition is subjected to tampering efforts, such as, for example, "street" extraction of the agonist component, whether by adulteration, distillation, or pulverization of a form of the composition. Such tampering efforts activate the safeguard mechanisms in the composition, as discussed in U.S. Pat. No. 5,922,705. Since each antagonist component is selected for its ability to competitively bind opiate receptors for a given route of administration (oral and parenteral) (U.S. Pat. No. 3,869,226), the act of tampering is ultimately rendered futile. Rather than obtaining an analgesic or euphoric state, any individual that tampers to "get high" will unleash a rapid detoxification treatment.

The present invention will be described in more detail with reference to the examples below, which should not be understood as limiting the invention in any way.

EXAMPLES

Example 1

A series of compositions for oral administration may be prepared containing oxycodone as the agonist component, a mixture of naltrexone and nalmefene as the antagonist component, and sennosides as the antagonist removal component. The components are present in the ranges shown in Table 1. An amount of antagonist up to 70 mg may also be used.

TABLE 1

Compositions for oral administration containing oxycodone as the agonist component, a mixture of naltrexone and nalmefene as the antagonist component, and sennosides as the antagonist removal component.*

| Oxycodone | Naltrexone | Nalmefene | Sennosides |
|---|---|---|---|
| 10 mg | 1.56-2.22 mg | 1 mg | 16 mg |
| 20 mg | 1.12-4.44 mg | 1 mg | 16 mg |
| 30 mg | 1.68-6.66 mg | 1 mg | 16 mg |
| 40 mg | 2.24-8.88 mg | 1 mg | 16 mg |
| 50 mg | 2.80-11.10 mg | 1 mg | 16 mg |
| 60 mg | 3.36-13.32 mg | 1 mg | 16 mg |
| 70 mg | 3.92-15.54 mg | 1 mg | 16 mg |
| 80 mg | 4.48-17.76 mg | 1 mg | 16 mg |
| 90 mg | 5.04-19.98 mg | 1 mg | 16 mg |
| 100 mg | 5.60-22.20 mg | 1 mg | 16 mg |
| 110 mg | 6.16-24.42 mg | 1 mg | 16 mg |
| 120 mg | 6.72-26.64 mg | 1 mg | 16 mg |
| 130 mg | 7.28-28.86 mg | 1 mg | 16 mg |
| 140 mg | 7.84-31.08 mg | 1 mg | 16 mg |
| 150 mg | 8.40-33.33 mg | 1 mg | 16 mg |
| 160 mg | 8.69-35.52 mg | 1 mg | 16 mg |

*The above compositions may be adjusted for such factors as age, weight, and general physical condition of the individual patient receiving the dosage.

Example 2

Another series of compositions for oral administration may be prepared containing oxycodone as the agonist component, nalmefene as the antagonist component, and bisacodyl, U.S.P. (United States Pharmacopeia) as the antagonist removal component. The components are present in the ranges shown in Table 2. Those skilled in the art will readily recognize that the amount of antagonist component in the compositions of Tables 1 and 2 may be adjusted depending on the nature of the agonist component, as is discussed in U.S. Pat. Nos. 6,132,416 and 6,214,379.

TABLE 2

Compositions for oral administration containing oxycodone as the agonist component, nalmefene as the antagonist component, and bisacodyl, USP as the antagonist removal component.*

| Oxycodone | Nalmefene | bisacodyl, USP |
|---|---|---|
| 10 mg | 1 mg | 16 mg |
| 20 mg | 1 mg | 16 mg |
| 30 mg | 1 mg | 16 mg |
| 40 mg | 1 mg | 16 mg |
| 50 mg | 1 mg | 16 mg |
| 60 mg | 1 mg | 16 mg |
| 70 mg | 1 mg | 16 mg |
| 80 mg | 1 mg | 16 mg |
| 90 mg | 1 mg | 16 mg |
| 100 mg | 1 mg | 16 mg |
| 110 mg | 1 mg | 16 mg |
| 120 mg | 1 mg | 16 mg |
| 130 mg | 1 mg | 16 mg |
| 140 mg | 1 mg | 16 mg |
| 150 mg | 1 mg | 16 mg |
| 160 mg | 1 mg | 16 mg |

*The above compositions may be adjusted for such factors as age, weight, and general physical condition of the individual patient receiving the dosage.

It should be understood that various changes and modifications to the preferred embodiments described herein will be apparent to those skilled in the art. Such changes and modifications can be made without departing from the spirit and scope of this invention and without diminishing its attendant advantages. It is therefore intended that such changes and modifications be covered by the appended claims.

I claim:

1. A composition for administration to a subject, the composition comprised of three components that have independent pharmaceutical potential and action to provide unobstructed narcotic analgesic action to a legitimate subject with moderate to severe pain, when taken as written and prescribed and absolutely no analgesic or euphoric potential and action once subjected to tampering and adulteration to liberate and isolate the narcotic component, wherein the composition consists of:
   (a) an immediate or time released narcotic agonist component;
   (b) a narcotic antagonist component comprising at least one antagonist, of comparable milligram and dosage potential of the agonist to negate any analgesic potential of the selected agonist, and to be sequestered and released, if and only if, the composition is subjected to tampering or adulteration; and
   (c) an immediate acting antagonist removal component from a group consisting of pharmaceutical agents, botanical agents, and mixtures thereof, to ensure the elimination of the sequestered antagonist component from the gastrointestinal tract of the subject, combined in a combination for oral administration in a formula creating a tamper-proof narcotic delivery system only when subjected to tampering and adulteration;
   wherein, the agonist having a narcotic effect is selected from and may be alfentanil, allylprodine, alphaprodine, anileridine, benzylmorphine, benzitramide, bupernorphine, butorphanol, clonitazcene, codeine, cyclazocine, desomorphine, dextromoramide, dexocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof or mixtures thereof, wherein the antagonist component is selected from the narcotic antagonist group and consisting of naltrexone, nalmefene, and a mixture thereof, wherein the antagonist removal component methylnaltrexone.

2. The composition of claim 1, wherein administration to the subject is oral administration.

3. The composition of claim 1, wherein the agonist component is an opioid agonist.

4. The composition of claim 1, wherein the agonist component is an immediate release agonist.

5. The composition of claim 1, wherein the agonist component has a delayed time of release.

6. The composition of claim 1, wherein the antagonist component is selected from the group consisting of naltrexone, nalmefene, and a mixture thereof.

7. The composition of claim 1, wherein the agonist component and the antagonist component are present in amounts such that the time release of the antagonist component and the time release of the agonist component are in a ratio of at least 4:1.

8. The composition of claim 7, wherein the agonist component is present in an amount ranging from about 10 mg to 160 mg, the antagonist component is present in an amount ranging from about 1.5 mg to about 70 mg, and the antagonist removal component is present in an amount of about 16 mg.

9. The composition of claim 7, wherein the agonist component is present in an amount ranging from about 10 mg to 160 mg, the antagonist component is present in an amount ranging from about 1 mg to about 70 mg, and the antagonist removal component is present in an amount of about 10-16 mg.

10. A method for the delivery to a subject, the method comprising the step of administering the composition to the subject as written and prescribed orally wherein the composition comprised of three components that have independent pharmaceutical potential and action to provide unobstructed narcotic analgesic action to a legitimate subject with moderate to severe pain, when taken as written and prescribed and absolutely no analgesic or euphoric potential and action once subjected to tampering and adulteration to liberate and isolate the narcotic component, wherein the composition consists of:

(a) an immediate or time released narcotic agonist component;

(b) a narcotic antagonist component comprising at least one antagonist, of comparable milligram and dosage potential of the agonist to negate any analgesic potential of the selected agonist and to be sequestered and released, if and only if, the composition is subjected to tampering or adulteration; and (c) an immediate acting antagonist removal component from a group consisting of pharmaceutical agents, botanical agents, and mixtures thereof, to ensure the elimination of the sequestered antagonist component from the gastrointestinal tract of the subject, combined in a formula for oral administration in a composition creating a tamper-proof narcotic delivery system only when subjected to tampering and adulteration;

wherein, the agonist having a narcotic effect is selected from and may be alfentanil, allylprodine, alphaprodine, anileridine, benzylmorphine, benzitramide, bupernorphine, butorphanol, clonitazcene, codeine, cyclazocine, desomorphine, dextromoramide, dexocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof or mixtures thereof, wherein the antagonist component is selected from the narcotic antagonist group and consisting of naltrexone, nalmefene, and a mixture thereof, wherein the antagonist removal component is methylnaltrexone.

11. The method of claim 10, wherein the composition is administered orally.

12. The method of claim 10, wherein the agonist component is an opioid agonist.

13. The method of claim 10, wherein the agonist component is an immediate release agonist.

14. The method of claim 10, wherein the agonist component has a delayed time of release.

15. The method of claim 10, wherein the antagonist component is selected from the group consisting of naltrexone, nalmefene, and a mixture thereof.

16. The method of claim 10, wherein the agonist component and the antagonist component are present in amounts such that the time release of the antagonist component and the time release of the agonist component are in a ratio of at least 4:1.

17. The method of claim 16, wherein the agonist component is present in an amount ranging from about 10 mg to 160 mg, the antagonist component is present in an amount ranging from about 1.5 mg to about 70 mg, and the antagonist removal component is present in an amount of about 16 mg.

18. The method of claim 16, wherein the agonist component is present in an amount ranging from about 10 mg to 160 mg, the antagonist component is present in an amount ranging from about 1 mg to about 70 mg, and the antagonist removal component is present in an amount of about 10-16 mg.

19. The method of claim 10, wherein the method comprises the step of administering the composition to the subject orally and further comprises the step of administering a potassium compound to the subject.

* * * * *

UNITED STATES PATENT AND TRADEMARK OFFICE
CERTIFICATE OF CORRECTION

PATENT NO.       : 7,968,119 B2                                    Page 1 of 1
APPLICATION NO.  : 10/183678
DATED            : June 28, 2011
INVENTOR(S)      : John Farrell It is certified that error appears in the above-identified patent and that said Letters Patent is hereby corrected as shown below:

Col. 7, line 4, should read:

wherein the antagonist removal component is methylnaltrexone.

Signed and Sealed this
Tenth Day of April, 2012

David J. Kappos
*Director of the United States Patent and Trademark Office*